US005217450A

United States Patent [19]

Pryor et al.

[11] Patent Number: 5,217,450

[45] Date of Patent: Jun. 8, 1993

[54] RETENTION DEVICES

[75] Inventors: Raymond J. Pryor; James F. Pharaoh, both of Hamilton, New Zealand

[73] Assignee: Carter Holt Harvey Plastic Products Group Limited, Hamilton, New Zealand

[21] Appl. No.: 831,732

[22] Filed: Feb. 10, 1992

Related U.S. Application Data

[63] Continuation of Ser. No. 554,930, Jul. 20, 1990, abandoned.

[30] Foreign Application Priority Data

Jul. 21, 1989 [NZ] New Zealand ........................ 230023

[51] Int. Cl.$^5$ ............................................. A61M 31/00

[52] U.S. Cl. ................................. 604/891.1; 604/107; 128/833; 606/198

[58] Field of Search ................ 606/198; 604/105-109, 604/174, 891.1; 128/830, 831, 833, 839

[56] References Cited

U.S. PATENT DOCUMENTS

| | | | |
|---|---|---|---|
| 1,819,828 | 8/1931 | Tomkinson . | |
| 2,010,457 | 8/1935 | Kanner | 604/107 |
| 2,649,092 | 8/1953 | Wallace | 604/105 |
| 3,397,699 | 8/1968 | Kohl | 604/105 |
| 3,911,911 | 10/1975 | Scommegna . | |
| 4,043,338 | 8/1977 | Homm et al. | 604/105 |
| 4,648,402 | 3/1987 | Santos | 606/198 |
| 4,660,571 | 4/1987 | Hess et al. | 604/105 X |
| 4,687,480 | 8/1987 | Laby et al. . | |
| 4,821,741 | 4/1989 | Mohajer . | |

FOREIGN PATENT DOCUMENTS

| | | | |
|---|---|---|---|
| 449029 | 3/1972 | Australia . | |
| 72442 | 4/1951 | Denmark | 606/198 |
| 271657 | 9/1913 | Fed. Rep. of Germany . | |
| 214913 | 5/1924 | United Kingdom | 604/106 |
| 2077103 | 12/1981 | United Kingdom . | |
| 2154875 | 9/1985 | United Kingdom . | |

*Primary Examiner*—Michael H. Thaler

*Attorney, Agent, or Firm*—Jacobson, Price, Holman & Stern

[57] ABSTRACT

A retention device which can be removably retained in a body cavity has branch members which are movably connected to each other such that two relative configurations may be obtained. In one configuration the branch members are nested inside one another for inserting the retention device in a cavity. Once in a cavity an operating member is used to displace the branch members to form the second configuration, in which parts of the branch members are expanded to bear against the walls of the cavity and retain the device.

8 Claims, 1 Drawing Sheet

RETENTION DEVICES

This is a continuation of application Ser. No. 07/554,930, filed Jul. 20, 1990 which was abandoned upon the filing hereof.

This invention relates to retention devices for removably retaining an object in a passage or cavity, and is intended particularly though not solely to provide a device which can be removably retained in a body cavity or passage, such as within the digestive or reproductive systems of an animal, for example for veterinary or reproduction control purposes.

It is an object of the invention to provide a retention device for removable retention in a passage or cavity which will at least provide the public with a useful choice.

Accordingly, in one aspect, the invention consists in a retention device for removable retention in a passage or cavity, comprising: a pair of bifurcated members each having a pair of resilient movable branch members the branch members of one bifurcated member being movably connected to the branch members of the other bifurcated member to form a diamond in one configuration of the pair; and an operating member connected or associated with one of said bifurcated members; said bifurcated members being displaceable between at least two relative configurations, a first configuration in which a first one of said bifurcated members is substantially nested inside the other of said bifurcated members for insertion purposes, and a second configuration being a laterally extended configuration in which parts of said bifurcated members are resiliently expanded to bear in use against walls of a selected passage or cavity to retain the device therein and said device is laterally compressible so as to be insertable into and removable from said passage or cavity, said device being displaceable between said configurations by use of said operating member.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Figure 1:
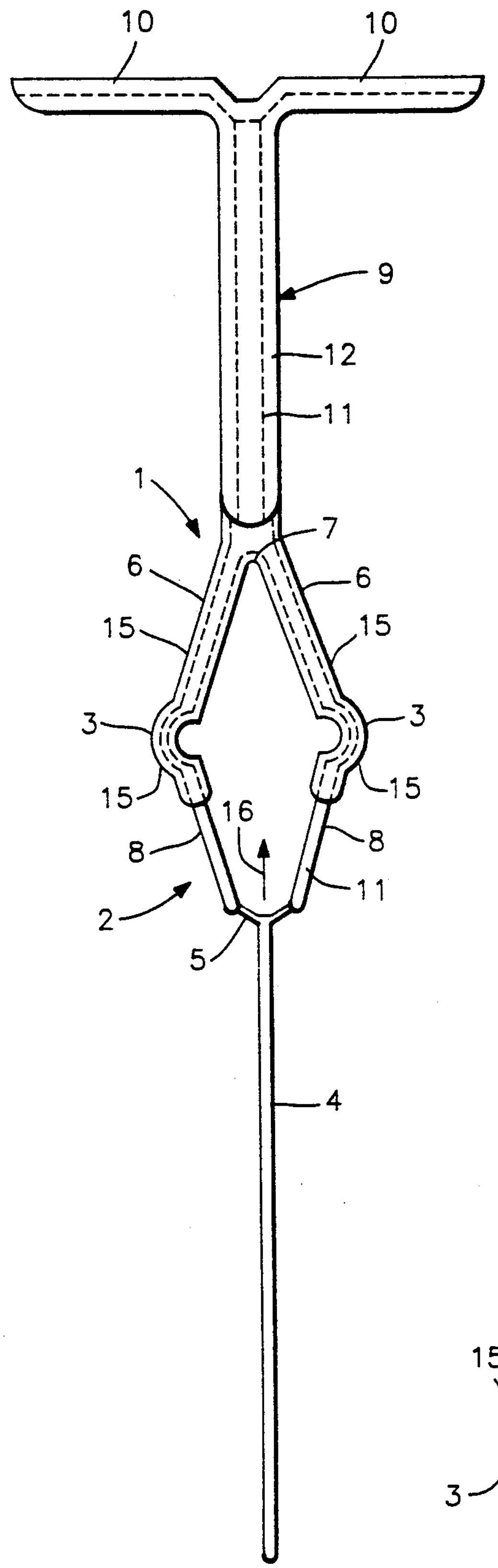
Figure 2:
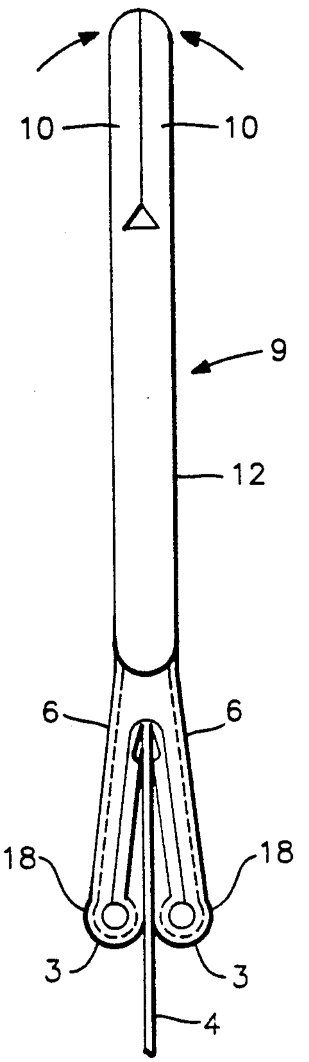
Figure 3:
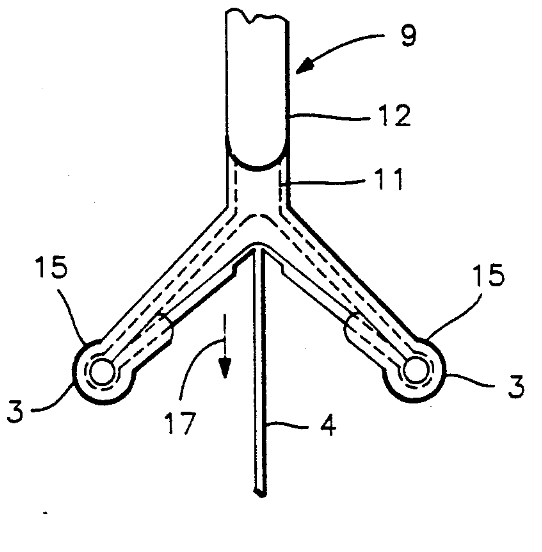

One preferred form of the invention will now be described with reference to the accompanying drawings, in which FIG. 1 shows a device in accordance with the invention in an open or diamond configuration;

FIG. 2 shows the device of FIG. 1 in an insertion configuration when laterally compressed for insertion into a selected passage or cavity; and FIG. 3 shows the device of FIGS. 1 and 2 in a retention configuration so as to be retained in the passage or cavity.

Referring now to the figures, a device for retention in a cavity or passage, such as in a body cavity or passage of animals such as cattle or pigs, is provided and shown in FIG. 1. The retention device comprises a pair of resilient movable bifurcated members, for example "V" or "U" shaped members 1 and 2 which are movably preferably resiliently interconnected at the open ends of the "V" or "U", for example by interconnections 3; and an operating member 4 is attached to or demountably associated with the junction or closed end 5 of the bifurcated member 2. Bifurcated member 1 has two preferably resiliently flexible branches 6, and bifurcated member 2 has two preferably resiliently flexible branches 8. The branches 6 are resiliently interconnected with one another at a junction 7 forming the closed end of bifurcated member 1 and the branches 8 are resiliently interconnected with each other at the junction 5 or closed end of bifurcated member 2. Branches 8 of bifurcated member 2 are suitably relatively shorter than equivalent branches 6 of bifurcated member 1 to enable nesting as shown in FIG. 2.

The retention device in use may be associated with or form part of a device for veterinary purposes and may then include some other functional portion such as a known device 9 having zones impregnated with a particular pharmaceutical to be dispensed to an animal, and having foldable legs 10 or any other desired functional portion.

The device may be moulded for example of a suitable plastics material which may be moulded in the configuration shown in FIG. 1 (referred to herein as the second configuration), and preferably comprises a skeleton 11 of a harder but still flexibly resilient material such as nylon or polypropeylene onto which a drug carrying matrix 12 of e.g. silicone or EVA is applied. Such a device 9 is disclosed in Patent Specifications GB2154875A and U.S. Pat. No. 4,678,463 which are incorporated herein by reference. Parts or all of branches 6 and 8 and parts or all of interconnections 3 are preferably coated with a cushioning layer 15 which is preferably a continuation of or of the same composition as the drug carrying matrix 12.

When it is desired to insert the device into a passage or cavity of an animal e.g. the vagina of a pig, the device may be folded, from the moulded second configuration shown in FIG. 1 in which the interconnection 3 of the bifurcated members 1 and 2 are spaced apart and so that the bifurcated members 1 and 2 are in a diamond configuration opposite one another into the insertion configuration shown in FIG. 2 by applying force to the operating member 4 towards the bifurcated members substantially along the longitudinal axis of the device, in the direction indicated by the arrow 16, so that the junction 5 of the bifurcated member 2 is forced towards the junction 7 of the opposite facing bifurcated member 1. Due to the pivoting and preferably resilience of the bifurcated members and of the connections 3 between them, initially the paired branches of the two bifurcated members are spread apart by application of such force, and when the relatively shorter branches 8 of member 2 are in line in the space between the interconnections 3, sprung over that line and nest with the branches 6 of the facing bifurcated member 1, as shown in FIGS. 2 and 3. The parts of the skeleton 11 forming the inter-connecting portions 3 are preferably provided as outwardly curved strips or portions of resilient material as shown to facilitate this springing over.

Once in the insertion configuration shown in FIG. 2, the device can be laterally compressed by pinching them together as indicated by the arrows 18, and the device 9, may also be folded. The entire device may be contained in this folded form in an applicator e.g. of tubular form as shown in GB2154875A, U.S. Pat. No. 4,678,463. The device is then inserted lengthwise into a selected passage or cavity, for example into a body cavity of an animal, and the applicator is then withdrawn. The branches 6 and 8 of the bifurcated members 1 and 2, when in the insertion configuration shown in FIG. 2, are biased to extend laterally from the longitudinal axis of the device, which can be defined by the longitudinal axis of the operating member 4, as shown in FIG. 3. When the applicator is withdrawn, the branches tend to adopt the laterally extended retention configuration shown in FIG. 3 and the device is thus retained against expulsion from the passage or cavity by for example muscular contractions, as the bifurcated members and/or the connecting portion 3 bear against the walls of the passage or cavity offering resistance to expulsion.

When it is desired to remove the device, the extended operating member 4 can be grasped and pulled in the direction indicated by the arrow 17 which reverses the springing over procedure, the bifurcated members 1 and 2 resuming their open and opposite facing configuration as shown in FIG. 1. Continued pulling on the operating member 5 tends to lead the device out of the passage or cavity, with extension lengthwise and narrowing the width of the diamond shape of the retention the device laterally compressing by closing of the branches 6 and 8 of bifurcated members 1 and 2 towards each other.

Thus it can be seen that a retention device is provided by the invention which is readily operated so as to be securely retained in a selected passage or cavity and which can also be readily converted into a configuration allowing withdrawal from the passage or cavity. The device is also simple to make and operate.

What is claimed is:

1. A retention device for removable retention in a passageway or cavity, comprising a first bifurcated member having a first junction and a first pair of resilient moveable branch members each extending from said first junction and each having a distal end; a second bifurcated member having a second junction and a second pair of resilient moveable branch members each extending from said second function and each having a distal end; the distal ends of each of said first pair of branch members being movably connected to corresponding distal ends of each of said second pair of branch members, said bifurcated members being displaceable into first, second and third configurations, the first configuration for insertion of said retention device in said passage or cavity having the branch members of said first bifurcated member substantially nested within the branch members of said second bifurcated member, said first junction in a first position adjacent said second junction and said moveable connections between said branch members adjacent to each other, the branch members of at least one of the bifurcated members being configured for biasing said connections outwardly from the first configuration toward the second configuration for retaining said retention device in said passage or cavity, the second configuration having the branch members of said first bifurcated member remaining substantially nested within the branch members of said second bifurcated member, said first junction in a second position which is further from said second junction than the first position and said moveable connections between said branch members being in a spaced apart relationship and being resiliently expanded towards said spaced configuration for engaging against walls of said passage or cavity, the third configuration having the branch members of said first bifurcated member no longer substantially nested within the branch members of said second bifurcated member but forming respective sides of a diamond for withdrawal of the device from the passageway or cavity, said device being displaceable from said second configuration to said third configuration wherein the second bifurcated member includes an elongated element extending away from said second junction in a direction opposite said branch members of the second bifurcated member and terminating in foldable legs axially spaced from said branch members of the second bifurcated member.

2. A retention device as claimed in claim 1 having flexible movable connections between said branches of said bifurcated members coated with a cushioning layer.

3. A retention device as claim in claim 1 wherein said retention device is associated with or forms part of a device for veterinary purposes.

4. A retention device as claimed in claim 1 wherein said branch members are flexibly resilient.

5. A retention device as claimed claim 1 wherein said branch members of bifurcated member are resiliently connected to corresponding branch members of the second bifurcated member.

6. A retention device as claimed in claim 1 wherein in the third configuration said first junction, said second junction, and said moveable connections between said branches form vertices of said diamond, and a distance between said first junction and said second junction is greater than a distance between said moveable connections.

7. A retention device as claimed in claim 1 including an elongate operating member attached to the first junction.

8. A retention device for removable retention in a passageway or cavity, comprising a first bifurcated member having a first junction and a first pair of resilient moveable branch members each extending from said first junction and each having a distal end; a second bifurcated member having a second junction and a second pair of resilient moveable branch members each extending from said second junction and each having a distal end; the distal ends of each of said first pair of branch members being movably connected to corresponding distal ends of each of said second pair of branch members, said bifurcated members being displaceable into first, second and third configurations, the first configuration for insertion of said retention device in said passage or cavity having the branch members of said first bifurcated member substantially nested within the branch members of said second bifurcated member, said first junction in a first position adjacent said second junction and said moveable connections between said branch members adjacent to each other, the branch members of at least one of the bifurcated members being configured for biasing said connections outwardly from the first configuration toward the second configuration for retaining said retention device in said passage or cavity, the second configuration having the branch members of said first bifurcated member remaining substantially nested within the branch members of said second bifurcated member, said first junction in a second position which is further from said second junction than the first position and said moveable connections between said branch members being a spaced apart relationship and being resiliently expanded towards said spaced configuration for engaging against walls of said passage or cavity, the third configuration having the branch members of said first bifurcated member no longer substantially nested within the branch members of said second bifurcated member but forming respective sides of a diamond for withdrawal of the device from the passageway or cavity, said device being displaceable from said second configuration to said third configuration wherein the second bifurcated members includes an elongated element extending away from said second junction and terminating in foldable legs, wherein an elongate operating member is attached to said first junction and wherein the operating member and said elongated element extend in opposite directions only from the respective junctions.

* * * * *